US009629885B1

United States Patent
Awaad et al.

(10) Patent No.: US 9,629,885 B1
(45) Date of Patent: Apr. 25, 2017

(54) METHOD FOR TREATING CANDIDIASIS

(71) Applicant: KING SAUD UNIVERSITY, Riyadh (SA)

(72) Inventors: Amani Shafeek Awaad, Riyadh (SA); Mohamed El-Desouky Zain, Riyadh (SA); Reham Mostafa El-Meligy, Riyadh (SA); Nour Khaled Al-Anazi, Riyadh (SA); Monerah Rashed Alothman, Alkharj (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 15/064,493

(22) Filed: Mar. 8, 2016

(51) Int. Cl.
*C07H 15/256* (2006.01)
*A61K 31/704* (2006.01)
*A61K 36/062* (2006.01)
*C12P 19/56* (2006.01)

(52) U.S. Cl.
CPC .......... *A61K 36/062* (2013.01); *A61K 31/704* (2013.01); *C07H 15/256* (2013.01); *C12P 19/56* (2013.01)

(58) Field of Classification Search
CPC .................. C07H 15/256; A61K 31/704
See application file for complete search history.

(56) References Cited

U.S. PATENT DOCUMENTS

2005/0014730 A1    1/2005  Carlson et al.

OTHER PUBLICATIONS

Proksch et al., "Sponge-associated fungi and their bioactive compounds: the Suberites case" Botanica Marina (2008) vol. 51 pp. 209-218.*
Qadri et al., "Identification and bioactive potential of endophytic fungi isolated from selected plants of the Western Himalayas" SpringerPlus (2013) vol. 2 No. 8 pp. 1-14.*
Vieira et al., "Diversity and antimicrobial activities of the fungal endophyte community associated with the traditional Brazilian medicinal plant Solanum cernuum Vell. (Solanaceae)" Canadian Journal of Microbiology (2012) vol. 58 pp. 54-66.*
Lou et al., "Endophytic fungi from medicinal herb *Salvia miltiorrhiza* Bunge and their antimicrobial activity," *Afr. J. Microbiol. Res.*, 2013, vol. 7, pp. 5343-5349.

* cited by examiner

*Primary Examiner* — Eric Olson
(74) *Attorney, Agent, or Firm* — Richard C. Litman

(57) ABSTRACT

A method for treating candidiasis includes administering to a human or animal subject in need thereof, a therapeutically effective amount of an anti-candidiasis compound. The anti-candidiasis compound can include 3β-diglucoside-5, 12-28-oic acid. The anti-candidiasis can be isolated from an extract of *Petriella setifera* or other *Petriella* species.

4 Claims, 4 Drawing Sheets

METHOD FOR TREATING CANDIDIASIS

BACKGROUND OF THE INVENTION

1. Field of the Invention

The present invention relates to treatment of candidiasis, and particularly to a method for treating candidiasis using a triterpenoidal compound isolated from an extract of a species of *Petriella*.

2. Description of the Related Art

*Candida* is defined as a genus of the unicellular fungi called yeasts. Candidiasis is a disease which varies from a mild superficial infection to a fulminating, deep-seated mycosis with a poor prognosis. Any defect in the immune system or changes in specific circumstances, can allow infection with *Candida*. Symptoms of candidiasis vary depending on the area affected. *Candida* species are frequently part of the human body's normal oral and intestinal flora. Treatment with antibiotics can lead to eliminating the yeast's natural competitors for resources. While many yeast species are harmless commensals or endosymbionts of hosts, including humans, other species, or even the harmless species in the wrong location, can cause disease. *Candida albicans*, for example, can cause infections (candidiasis or thrush), especially in immunocompromised patients.

Candidiasis is commonly treated with antimycotics. Some treatment options for invasive candidiasis include for example, fluconazole, voriconazole, and amphotericin B and its lipid formulations, as well as echinocandins, Voriconazole, amphotericin B, Amphotericin B lipid formulations, caspofungin, itraconazole, and posaconazole are available for the treatment of invasive aspergillosis. Additional procedures, such as surgical interventions, immunoregulatory therapy and granulocyte transfusions have also been used.

While *Candida* infections are generally not fatal; certain forms can be fatal. For example, in the case of blood infections caused by *Candida* (usually *Candida albicans*), the mortality rate is about 40%. Fungal secondary metabolites have a wide range of chemical structure and biological activities. They are derived from many different intermediates by special enzymatic pathways. Fungal secondary metabolites or biochemical indicators of fungal development are of intense interest to humankind due to their pharmaceutical and/or toxic properties.

Recently, two new butyrolactone I derivatives were isolated from a strain of *Aspergillus terreus* Thom (Trichocomaceae) isolated from desert soil. The anti-fungal activities of both intra and extra cellular metabolites of *A. terreus* grown on yeast extract sucrose and malt extract media were determined. The metabolites of *A. terreus* grown on yeast extract sucrose medium were found to be active against *Aspergillus fumigatus* RCMB 002008. The anti-fungal activity of *A. terreus* was attributed to the presence of two compounds whose minimum inhibitory concentrations (MIC) against *A. fumigatus* were found to be 32 and 16 mg/ml, respectively.

Thus, a compound for treating candidiasis solving the aforementioned problems is desired.

SUMMARY OF THE INVENTION

A method for treating candidiasis can include administering to a patient in need thereof a therapeutically effective amount of an anti-candidiasis compound. The anti-candidiasis compound can be 3β-diglucoside-5, 12-28-oic acid, which is represented by the following formula:

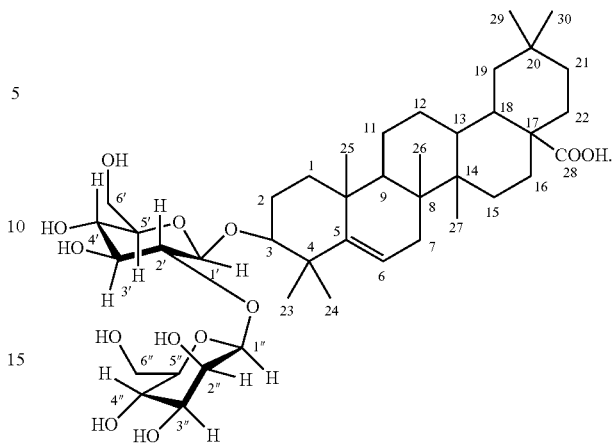

The anti-candidiasis compound for treating candidiasis can be isolated from an extract of a species of the *Petriella* genus. The anti-candidiasis compound can be isolated from an alcoholic extract of *Petriella setifera*, for example. The anti-candidiasis compound can be obtained by growing a mat of *Petriella* on malt extract, and percolating the mat in alcohol to provide a crude *Petriella* extract. The crude extract can be optionally concentrated under reduced pressure to provide a solid extract. The crude *Petriella* extract can be subjected to solvent fractionation using an organic solvent. The solvent fractions can be further fractionated by Sephadex column chromatography followed by silica gel column chromatography.

Candidiasis can be treated by administering a therapeutically effective amount of the anti-candidiasis compound to a subject suffering from candidiasis. The candidiasis can be caused by an infection from a species of *Candida*. The *Candida* species can include at least one of *C. albicans, C. dubliniensis, C. famata, C. glabrata, C. inconspicua, C. kefyr, C. krusei, C. norvegensis, C. parapsilosis* and *C. tropicalis*.

These and other features of the present invention will become readily apparent upon further review of the following specification.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
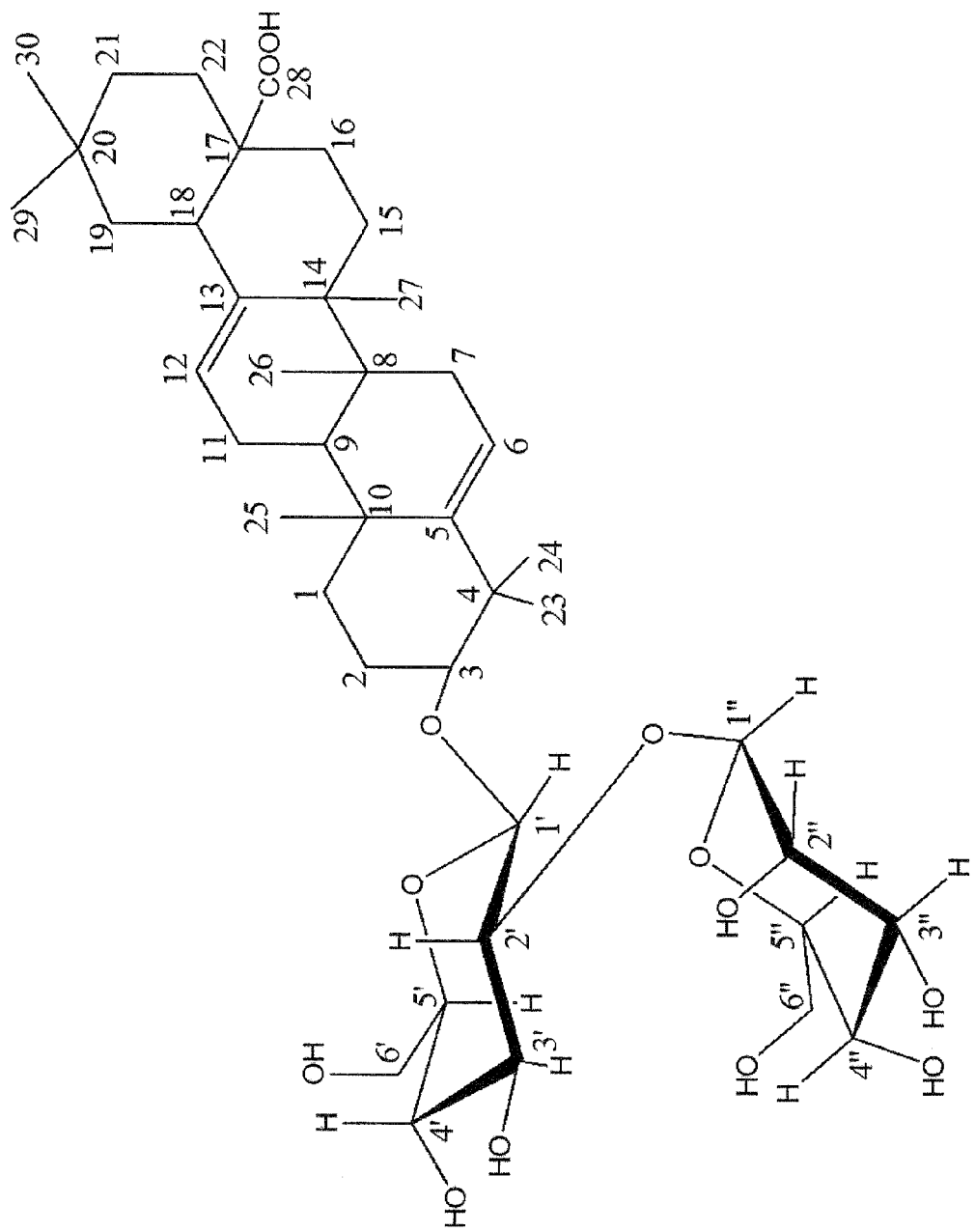
FIG. 1 shows the structural representation of Amnomopin (3β-diglucoside-5, 12-28-oic acid) isolated from the extract of *Petriella setifera*.

A method for treating candidiasis includes administering to a human or animal subject in need thereof, a therapeutically effective amount of an anti-candidiasis compound. The anti-candidiasis compound can include 3β-diglucoside-5, 12-28-oic acid, which is represented by the following structural formula:

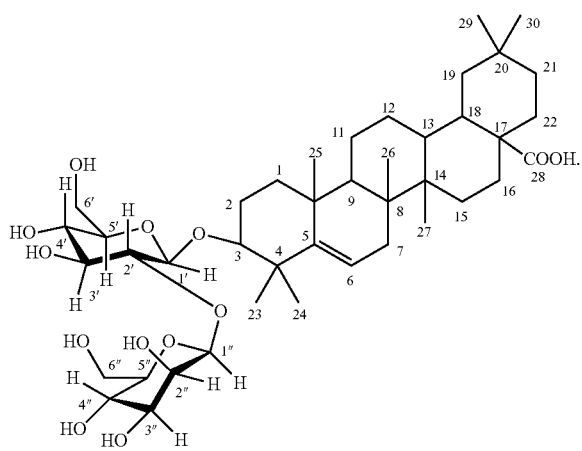

The anti-candidiasis compound is a triterpenoidal compound, and is also referred to herein as "amnomopin." The anti-candidiasis compound can be isolated from an extract of *Petriella setifera* or other *Petriella* species. The anti-candidiasis compound can be obtained by growing a mat of *Petriella setifera* on malt extract, and percolating the mat in alcohol to provide a crude *Petriella setifera* extract. The alcohol can be at least one of ethanol and methanol. The crude extract can be optionally concentrated under reduced pressure to provide a solid extract. The *Petriella setifera* extract can be subjected to solvent fractionation using an organic solvent. The organic solvent can be at least one of chloroform, ether, and methanol. The solvent fractions can be further fractionated by Sephadex column chromatography followed by silica gel column chromatography to provide the anti-candidiasis compound.

The anti-candidiasis compound can be an active agent in a composition for treating candidiasis. The composition can include, for example, an alcohol extract of *Petriella setifera*, as described herein, including the anti-candidiasis compound. A composition including the anti-candidiasis compound can include one or more pharmaceutically acceptable carriers. Carriers are inert pharmaceutical excipients, including, but not limited to, binders, suspending agents, lubricants, flavorings, sweeteners, preservatives, dyes, and coatings. In preparing compositions in oral dosage form, any of the pharmaceutical carriers known in the art may be employed. For example, for liquid oral preparations, suitable carriers and additives include water, glycols, oils, alcohols, flavoring agents, preservatives, coloring agents and the like; for solid oral preparations, suitable carriers and additives include starches, sugars, diluents, granulating agents, lubricants, binders, disintegrating agents and the like. For parenteral use, the carrier will usually comprise sterile water, though other ingredients, for example, for purposes such as aiding solubility or for preservation, may be included. Injectable suspensions may also be prepared, in which case appropriate liquid carriers, suspending agents and the like may be employed. Accordingly, the pharmaceutically acceptable carrier can include alcohol, dimethyl sulfoxide (DMSO), a physiological saline, a lipid based formulation, a liposomal formulation, a nanoparticle formulation, a micellar formulation, a water soluble formulation, a biodegradable polymer, an aqueous preparation, a hydrophobic preparation, a lipid based vehicle, or a polymer formulation.

The anti-candidiasis compound or compositions including the anti-candidiasis compound can be administered to a subject by any suitable route for treating candidiasis. Parenteral, otic, ophthalmic, nasal, inhalable, buccal, sublingual, enteral, topical, oral, peroral, and injectable dosage forms are particularly useful. Particular dosage forms include a solid or liquid dosage forms. Exemplary suitable dosage forms include tablet, capsule, pill, caplet, troche, sache, solution, suspension, dispersion, vial, bag, bottle, injectable liquid, i.v. (intravenous), i.m. (intramuscular) or i.p. (intraperitoneal) administrable liquid and other such dosage forms known to the artisan of ordinary skill in the pharmaceutical sciences.

The amount of the anti-candidiasis compound incorporated in a dose can be selected according to the examples provided herein and/or according to known principles of pharmacy. An effective amount or therapeutically effective amount of the anti-candidiasis compound is specifically contemplated. By the term "effective amount", it is understood that, with respect to, for example, pharmaceuticals, a pharmaceutically effective amount is contemplated. A pharmaceutically effective amount is the amount or quantity of active ingredient which is enough for the required or desired therapeutic response, or in other words, the amount, which is sufficient to elicit an appreciable biological response when, administered to a patient. The appreciable biological response, i.e., anticandidal activity, can occur as a result of administration of single or multiple doses of an active substance. A dose may comprise one or more dosage forms. It will be understood that the specific dose level for any patient will depend upon a variety of factors including the indication being treated, severity of the indication, patient health, age, gender, weight, diet, pharmacological response, the specific dosage form employed, and other such factors. According to an embodiment, about 500 mg/kg of an alcoholic extract of *Petriella setifera* can be administered orally to a subject in need thereof for a period of about 15 days. According to an embodiment, about 50 mg/kg of the anti-candidiasis compound can be administered orally to a subject in need thereof for a period of about 15 days.

A therapeutically effective amount of the anti-candidiasis compound or extract of *Petriella setifera* can be administered to a subject in need thereof to reduce and/or inhibit candidiasis infection caused by at least one of *C. albicans, C. dubliniensis, C. famata, C. glabrata, C. inconspicua, C. kefyr, C. krusei, C. norvegensis, C. parapsilosis* and *C. tropicalis*.

A *Petriella* alcoholic extract can be prepared by growing *Petriella* on malt extract; extracting the *Petriella* by percolation using alcohol to obtain an alcohol extract; and optionally concentrating the extract under reduced pressure to obtain a solid extract. The percolation step can be performed at least four times and the alcohol extracts can be combined and concentrated under reduced pressure to obtain a dry extract.

The present teachings will be understood more readily by reference to the following examples, which are provided by way of illustration.

Example 1

Fungal Isolation

The fungal strain was isolated from a soil sample collected from Al-Qassim region, Kingdom of Saudi Arabia (KSA). The malt extract agar (MEA) medium (malt extract, 20 g; peptone, 1 g; dextrose, 20 g; agar, 20 g; distilled water, 1 L) was used for isolation, cultivation, identification and production of fungal secondary metabolites of the fungal isolate and test *Candida* species. Ten clinically isolated *Candida* species; namely, *Candida albicans, C. dubliniensis, C. famata, C. glabrata, C. inconspicua, C. kefyr, C. krusei, C. norvegensis, C. parapsilosis*, and *C. tropicalis* were used as test microorganisms. The fungal isolate and the test organism were identified at the Microbiology Laboratory, Regional Center for Mycology and Biotechnology, Al-Azhar University, Cairo, Egypt.

Example 2

Extraction

A mat (700 g) of *Petriella setifera*, grown on malt extract, was extracted by percolation in ethanol (2 L) at room temperature for two days and then filtered. The residue was re-percolated again and the process repeated for about four times until complete extraction. The five ethanol extracts were combined and concentrated under reduced pressure at a temperature not exceeding 35° C. to yield a dry extract (120 g) after removal of the alcohol.

Example 3

Anticandidal Activity Determination

Anticandidal activities of total alcoholic extract of *Petriella setifera* and the isolated compound (amnomopin) were determined using well-diffusion method according to Zain et al. (2012). Petri plates containing 20 ml of malt extract agar medium were seeded with 48 h cultures of candidal inoculums (1-2×10$^7$ Colony Forming Units [CFU/ml]). Wells (6 mm in diameter) were cut off into agar and 50 µl of extract and the isolated compound were tested in a concentration of 100 mg/ml and incubated at 37° C. for 24-48h. The assessment of anticandidal activity was based on measurement of the diameter of the inhibition zone formed around the well.

The anticandidal activity of the extract of *Petriella setifera* (Amnomopin) was tested against clinically isolated *Candida* species. The total alcohol extract and the isolated compound showed significant activity against all of the investigated *Candida* species; namely, *C. albicans, C. dubliniensis, C. famata, C. glabrata, C. inconspicua, C. kefyr, C. krusei, C. norvegensis, C. parapsilosis, C. tropicalis*. The highest anticandidal activity of the total alcohol extract was obtained against *C. kefyr* (22.6+1.5 mm, 00.98 µg/ml), *C. albicans* and *C. norvegensis* (21.3+0.63 mm, 01.95 µg/ml), and *C. krusei* (20.6+1.5 mm, 01.95 µg/ml), while the lowest activity (14.2±1.20 mm, 62.50 µg/ml) was obtained against *C. glabrata*.

Example 4

Minimum Inhibitory Concentration (MIC)

The minimum inhibitory concentration (MIC) was determined for both total extract of *Petriella setifera* and the isolated compound by micro-dilution method using serially diluted (2 folds) according to Awaad et al. (2012). The MIC was determined by dilution of total extract and isolated compound of concentrations of 0.0-1000 µg/ml. Equal volume of each extract and malt extract broth were mixed in a test tube. Specifically, 0.1 ml of standardized inoculum (1-2×10$^7$ CFU/ml) was added in each tube. The tubes were incubated at 37° C. for 24-48 h. Two control tubes; tube containing the growth medium, saline and the inoculum, were maintained for each test batch. The lowest concentration (highest dilution) of the extract that produced no visible candidal growth (no turbidity) when compared with the control tubes were regarded as MIC.

Example 5

Isolation of Active Compound "Amnomopin"

3β-diglucoside-5, 12-28-oic acid

Forty-two grams of the intracellular alcoholic extract of *Petriella setifera* was applied on top of glass column (5 cm×150 cm) packed with Sephadex (120 g) and eluted with methanol. Two hundred fractions (60 ml each) were collected and chromatographed on thin layer chromatography (TLC) using two different solvent systems [a; ether-methanol 95:5 v/v & b; chloroform-ether 50:50 v/v] and investigated under UV before and after spring with antimony trichloride (SbCl$_3$). Similar fractions with the same number of spots color and Rf values were combined together and reduced to two main sub-fractions (A & B). The two sub-fractions were each subjected to further purification using glass column (1.5×60 cm) packed with silica gel (20 g) and eluted using ether: chloroform (9:1 v/v), from which compound (NRB) was isolated and identified using different spectroscopic analysis.

Figure 2:
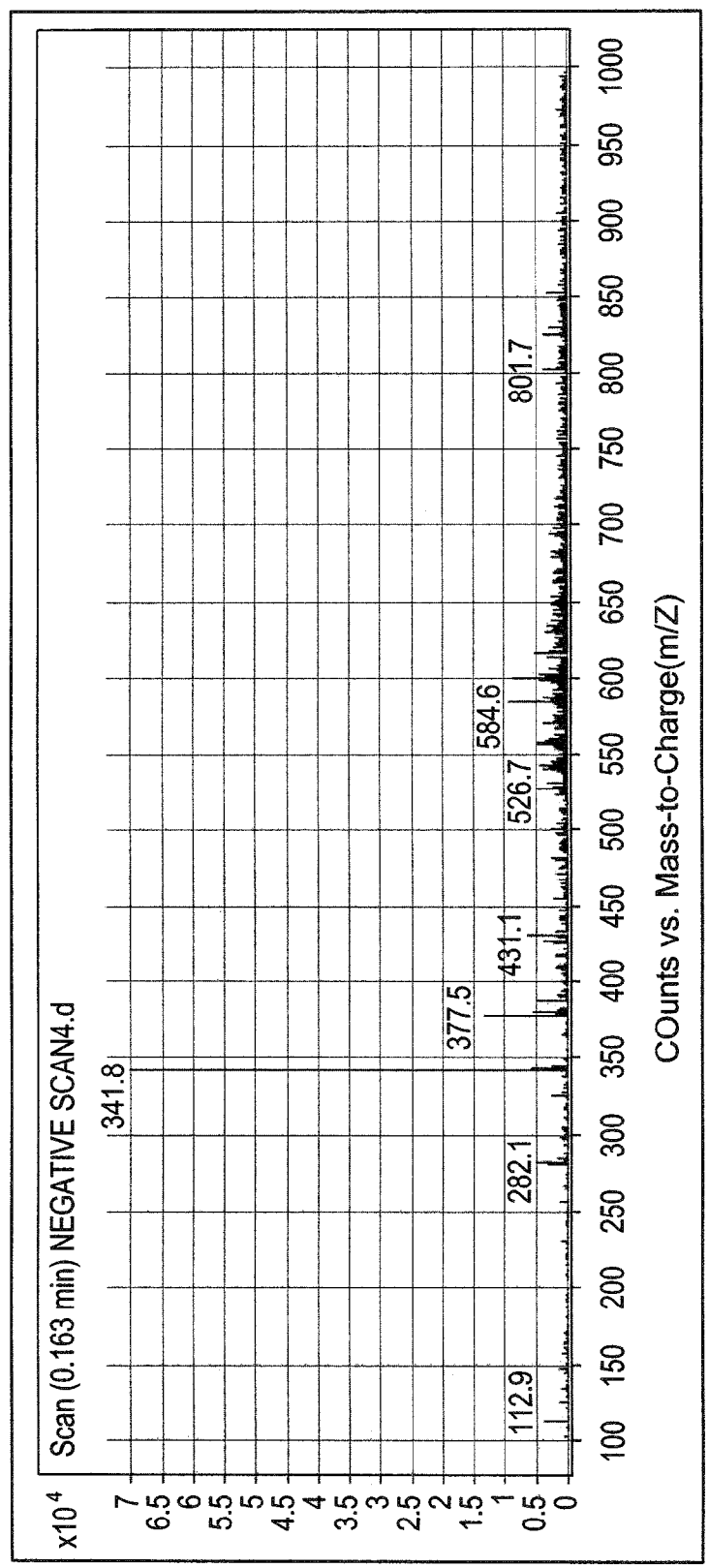
FIG. 2 shows the mass spectrum of the compound Amnomopin isolated from *Petriella setifera*.

The isolated compound was obtained as white crystals (750 mg). The retention factor was found to be Rf=0.60 in chloroform: ether (50:50 v/v) and a melting point (m.p.) of 257-258° C. As shown in FIG. 2, the ESI-MS negative ion mode spectrum of compound HAC showed an ion peak at m/z 801 [M+Na]+(5%), suggesting a molecular weight of 778 equal to molecular formula $C_{42}H_{66}O_{13}$. The ESI-MS positive ion mode revealed the presence of an intense ion peak at 588 corresponding to [M-162-CO] and 572 corresponding to [M-162-COO].

Figure 3:
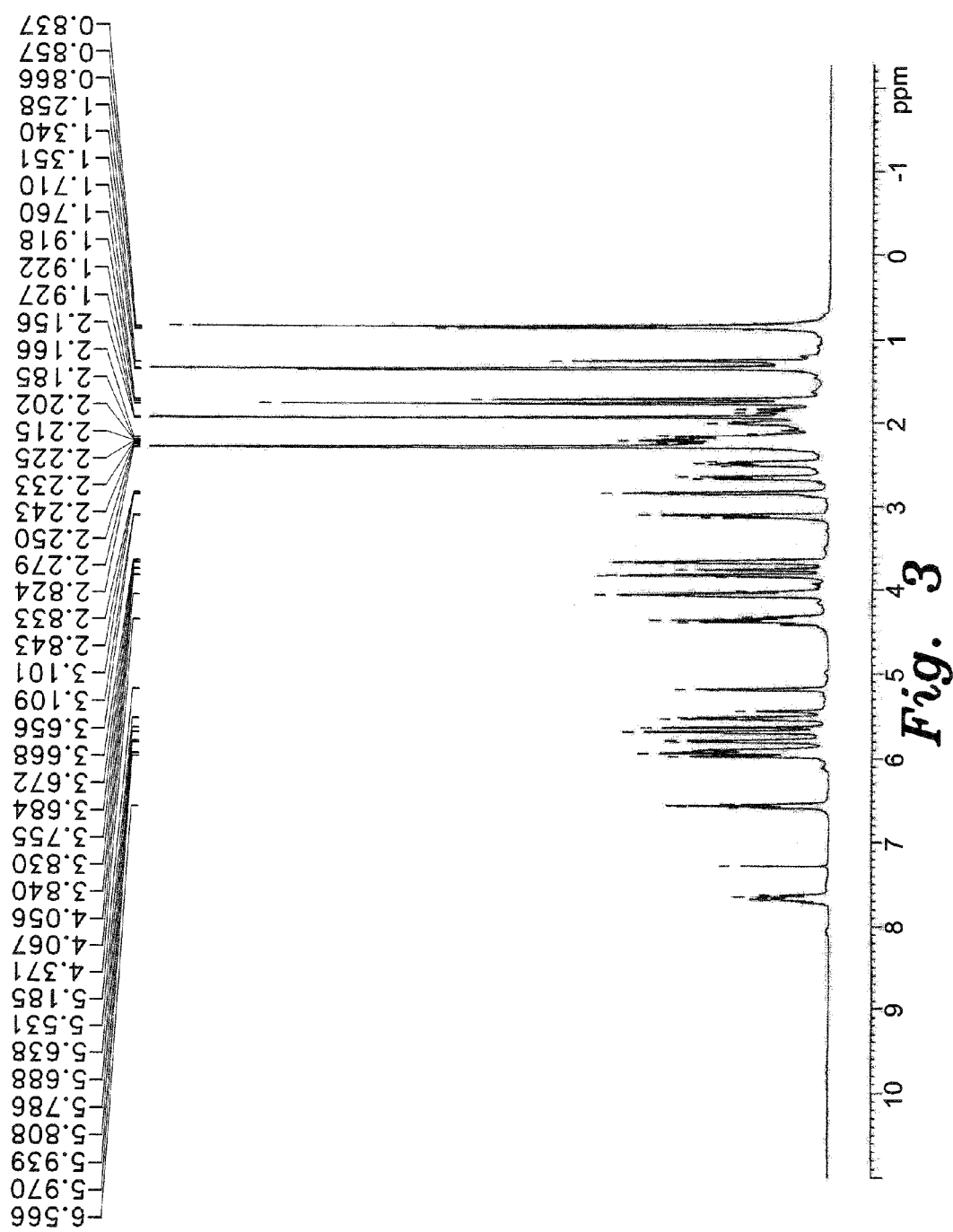
FIG. 3 shows the $^1$H-NMR of the Amnomopin compound isolated from *Petriella setifera*.

The $^1$H-NMR (CDCl$_3$) spectrum as shown in FIG. 3 showed signals in δ unit as the following: Two olefinic protons at δ 5.06 H-12, δ 6.54 d, J=5.2, 9.5 Hz, H-6, Seven CH$_3$ groups at δ 0.86 brs, 3H-30, δ 0.84 brs, 3H-29, δ 1.20 brs, 3H-27, δ 0.69 brs, 3H-26, δ 0.62 brs, 3H-25, δ 0.88 brs, 3H-24, δ 0.91 brs, 3H-23, δ 3.09 dd, J=9.5, 5.5 Hz, H-3. Nine methylene protons as several multiplets located between δ 2-3.1 linked to C-1, 2, 7, 11, 15, 16, 19, 21 and C-22 respectively. The anomeric sugar H-1' as d at δ 5.76, J=7.76 Hz, H-1" at δ 5.5 as d, J=7.76 Hz, H-2' is located down field at δ 4.05 as d, J=7 Hz, H-2" at δ 4.34 d, J=7 Hz, δ 3.10 dd, J=4.03, 5.50 Hz, H-3' &. H-3", δ 3.08 dd, J=5.49, 5.5 Hz, H-4' & H-4", δ 3.20 d, J=4.3 Hz, H-5'& H-5", δ 3.60 H-6'a δ 3.62 H-6'b.

Figure 4:
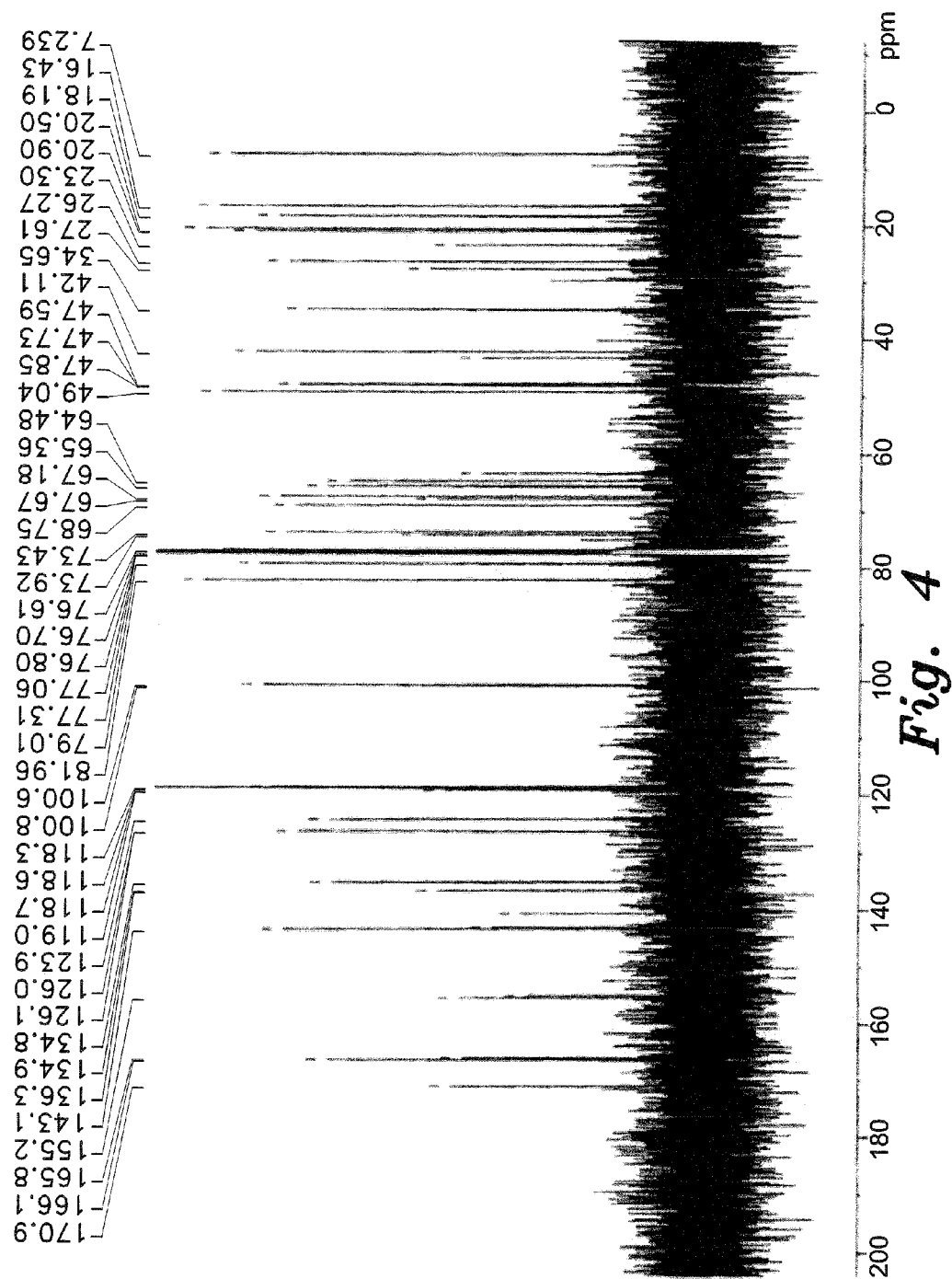
FIG. 4 shows the $^{13}$C-NMR of the Amnomopin compound isolated from *Petriella setifera*.

As shown in FIG. 4, the $^{13}$C-NMR (CDCl$_3$) spectral data indicated 42 carbon signals. The oleanolic acid moiety C-28 is located at δ 170.9, while C—O carbon at δ C-3 is located at δ 79.9 due to glycosylation. Olefinic carbons at 143.1, 121.9, 123.9, 142.6, are tentatively assigned for C-5, C-6, C-12 and C-13. The Dept. experiment showed seven methyl groups at δ 16.4, 18.1, 18.3, 20.5, 20.9 and 23.3, which are attributed tentatively to C-30, C-29, C-24, C-23, C-25, C-26 and C-27 atoms. It also exhibited nine CH2-carbons at δ 26, 34.6, 34.8, 47.5, 47.7, 47.8, 42.1, 43.1 and 27.6 respectively, which are tentatively assigned for C-1, C-2, C-7, C-11, C-15, C-16, C-21, C-22 and C-19 atoms. The δ at 50.1 and 49.9 are assigned tentatively to C-9 and C-14 respectively.

The two sugar moieties of Amnomopin showed their carbons at δ 100.8, 100.6, 79.1, 81.9, 73.9, 73.9, 67.1, 68.7, 76.6, 76.6, 63.1, 64.4, which are attributed to C-1', C-1", C-2', C-2", C-3", C-4', C-4", C-5', C-5", C-6', C-6" respectively.

The 13C-NMR (CDCl3) spectral data indicated 41 C signals were observed. The oleanolic acid moiety C-28 is located at δ 170.9, while C—O carbon at δ C-3 is located at δ 79.9. Seven methyl groups were appeared at δ 16.41, 18.1, 18.3, 20.5, 20.9 and 23.3 attributed to C-29, C-30, C-23, C-24, C-10, and 8 respectively. The experiment showed 9 CH2-carbons at δ 26, 34.6, 34.8, 47.5, 47.7, 47.8, 42.1, 43.1 and 27.6. For C-1, C-2, C-7, C-11, C-15, C-16, C-21, C-22 and C-19 respectively. The rest of the methine carbon was present between 15-45.

Example 6

Total Acid Hydrolysis

The isolated compound NRB (10 mg) was subjected to acid hydrolysis using 0.1N HCl for 1 h. The aqueous extract was then neutralized using barium carbonate and filtered off. The filtrate was extracted with ethyl acetate to separate the aglycone moiety from the glycone. Ethyl acetate extract was concentrated and treated the shift reagents then subjected to UV, $^1$H-NMR and $^{13}$C-NMR. On analyzing the obtained results, a compound the free aglycone was identified, which has been identified before. The aqueous layer containing glycone was tested on thin layer chromatography (TLC) alongside with sugars using the system ethyl acetate-methanol-acetic acid-water (65:15:10:10, v/v/v/v) and sprayed with naphthoresocinol-sulphuric acid resulting in glucose.

Example 7

Controlled Acid Hydrolysis

Controlled acid hydrolysis of compound NRB was carried out using 0.2 N HCl reflux for 1 h, traced every 5 min and examined using PC and TLC as mentioned before. After 25 min triterpine-O-glucoside in addition to free triterpine and glucose were obtained indicating that the terminal sugar is also glucose. From the above results, the compound NRB (3β-diglucoside-5, 12-28-oic acid) was found to be a novel compound, which was named commonly as "Amnomopin" having the chemical structure depicted in FIG. 1.

Example 8

Anticandidal Activity of the Isolated Compound "Amnomopin"

The amnomopin compound showed greater anticandidal activity than the total extract. The anticandidal activity of the amnomopin compound was tested against clinically isolated Candida species and the results were compared against amphotericin B. As shown in Table 1, the isolated compound showed anticandidal activity against all of the investigated Candida species; namely, C. albicans, C. dubliniensis, C. famata, C. glabrata, C. inconspicua, C. kefyr, C. krusei, C. norvegensis, C. parapsilosis, C. tropicalis. The highest anticandidal activity of the isolated compound was against C. kefyr (24.2±2.10 mm, 00.49 µg/ml), C. albicans (23.1±2.10 mm, 00.49 µg/ml) and C. norvegensis (22.1±1.20 mm, 00.98 µg/ml). Surprisingly, the anticandidal activity of the isolated compound (24.2±2.10 mm, 00.49 µg/ml) was almost similar to the activity of the standard antibiotics (amphotericin B) (26.3±1.20 mm, 00.49 µg/ml) against C. kefyr.

TABLE 1

Anticandidal activity of the compound (Amnomopin) isolated from Petriella setifera

| Candida sp. | Diameter of inhibition zone (mm) | | Minimum Inhibitory Concentration (MIC) (µg/ml) | |
|---|---|---|---|---|
| | Amnomopin | Amphotericin B | Amnomopin | Amphotericin B |
| C. albicans | 23.1 ± 2.10 | 26.3 ± 1.20 | 01.95 | 00.49 |
| C. dubliniensis | 16.2 ± 0.63 | 24.1 ± 1.20 | 62.50 | 00.49 |
| C. famata | 20.1 ± 1.50 | 20.4 ± 0.63 | 03.90 | 03.90 |
| C. glabrata | 16.3 ± 0.63 | 19.3 ± 2.10 | 62.50 | 03.90 |
| C. inconspicua | 18.3 ± 2.10 | 21.9 ± 1.20 | 32.25 | 00.98 |
| C. kefyr | 24.2 ± 2.10 | 26.3 ± 1.20 | 00.98 | 00.49 |
| C. krusei | 20.9 ± 0.58 | 23.7 ± 0.63 | 01.95 | 00.98 |
| C. norvegensis | 22.1 ± 1.20 | 28.7 ± 0.72 | 01.95 | 00.49 |
| C. parapsilosis | 18.4 ± 0.72 | 32.4 ± 0.58 | 32.25 | 00.49 |
| C. tropicalis | 19.4 ± 1.20 | 19.6 ± 1.50 | 07.81 | 03.90 |

Example 9

Determination Acute Toxicity ($LD_{50}$) Test

The oral median lethal dose ($LD_{50}$) of the total alcoholic extract of the investigated test organisms was determined as described by Lorke (1983). Swiss albino mice (both sex 26-30 g) in groups of six, received one of 500, 1000, 2000, or 5000 mg/kg doses of the tested extract. Control animals received the vehicle only and were kept under the same conditions. Signs of acute toxicity and number of deaths per dose within 24 h were recorded.

The alcoholic extract of Petriella setifera was characterized by a low degree of toxicity. The obtained results indicated that different doses of the alcohol of extract (500, 1000, 2000 and 5000 mg/kg) did not produce any symptom of acute toxicity and none of the mice died during 24 h of observation. It was suggested that oral $LD_{50}$ were higher than 5000 mg/kg. Since substances possessing $LD_{50}$ higher than 50 mg/kg are non-toxic (Awaad et al. 2014), the tested extracts were considered safe.

Example 10

Determination Sub-Chronic Toxicity Test

Male Wister rats (weighing about 150-180 g) were divided into 3 equal groups each of 10 rats. Rats of the first group received the vehicle in a dose of 5 mL/kg and left as normal control. Rats of the second and third groups were administered the alcoholic extract of the investigated fungi (500 mg/kg) and the isolated compound (50 mg/kg). All medications were administered orally daily for 15 consecutive days. Animals were maintained under identical conditions with food and water ad libitum for the entire period with close observation. At the end of the experimental period, blood samples were collected from the orbital plexus of rats, 6 h after the last dose. Samples were left to clot at room temperature for 20 min. The obtained sera were collected and used to determine the activity of (AST) aspirate aminotransferase and (ALT) alanine aminotransferase, levels of urea and creatinine were also estimated (Awaad et al. 2014).

The effect of the total alcohol extract of *Petriella setifera* and isolated compound (Amnomopin) on liver and kidney functions are provided in Table 2. Three groups of animals (n=10) were orally administered the total alcohol extracts (500 mg/kg) and the isolated compound (50 mg/kg) daily for 15 days, while the control group received water orally. After the treatment period, blood samples were collected, sera were separated and different parameters were measured as provided in Table 2. All values were expressed as mean±S.D.

TABLE 2

| Treatment | Liver function (U/l) | | Kidney function (mg/dl) | |
| --- | --- | --- | --- | --- |
| | AST | ALT | Blood urea | Serum Creatinine |
| Control | 66.11 ± 2.61 | 144.62 ± 5.39 | 32.16 ± 1.83 | 0.36 ± 0.03 |
| Alcoholic extract (500 mg/kg) | 65.39 ± 2.25 | 146.50 ± 4.27 | 33.40 ± 1.96 | 0.37 ± 0.03 |
| Amnomopin (50 mg/kg) | 66.72 ± 2.82 | 146.30 ± 4.30 | 30.85 ± 1.83 | 0.38 ± 0.02 |

The non-toxic nature of the total alcohol extract of the investigated fungi in acute toxicity study is well supported by the results of sub-chronic toxicity study. Oral dosing of the *Petriella setifera* (500 mg/kg) and the isolated compound NRB (50 mg/kg) for 15 days did not show any significant effect on the activity of ALT, AST and the levels of blood urea and serum creatinine as shown in Table 2 above.

The serum transaminase level is most widely used as a measure of hepatic injury, due to its ease measurement and high degree of sensitivity. It is useful for the detection of early damage of hepatic tissue. Since the activity of (ALT) alanine aminotransferase and (AST) aspirate aminotransferase are specific assayable liver enzymes, their normal levels in serum of rats treated for 15 days means that the investigated extract is not hepatotoxic.

Urea and creatinine are the most sensitive biochemical markers employed in the diagnosis of renal damage. In kidney damage, there will be retention of urea and creatinine in the blood (Nwanjo et al. 2005), therefore marked increase in serum urea and creatinine are indications of functional damage to the kidney. By these indicators, the investigated extract is therefore, not nephrotoxic in rats.

It is to be understood that the present invention is not limited to the embodiments described above, but encompasses any and all embodiments within the scope of the following claims.

We claim:

1. A method for treating candidiasis, comprising administering to a subject in need thereof an effective amount of an anti-candidiasis compound, the anti-candidiasis compound including 3β-diglucoside-5, 12-28-oic acid, represented by the following formula

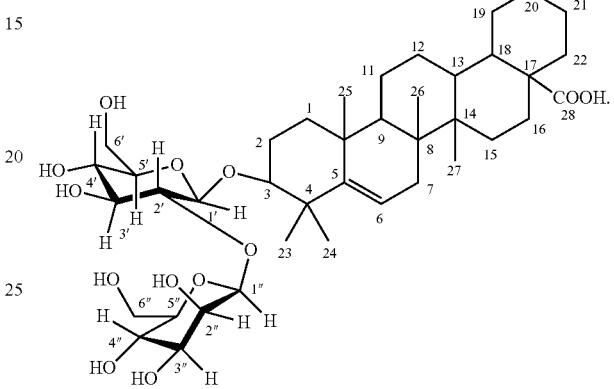

2. The method for treating candidiasis according to claim 1, wherein the anti-cadidiasis compound is isolated from an extract of *Petriella setifera*.

3. The method for treating candidiasis according to claim 1, wherein the anti-cadidiasis compound is included in an extract of *Petriella setifera*.

4. A method of preparing an extract of a species of *Petriella*, comprising:
 growing a species of *Petriella* on malt extract;
 extracting the species of *Petriella* by percolation with alcohol to obtain an alcoholic extract;
 concentrating the extract under reduced pressure to obtain a solid extract;
 wherein the percolation step is performed at least four times and
 wherein the *Petriella* species is *Petriella setifera*.

* * * * *